United States Patent
Mitchell

(10) Patent No.: US 9,345,587 B2
(45) Date of Patent: May 24, 2016

(54) PIVOTAL LATERAL CAGE AND METHOD OF INSERTION

(71) Applicant: Beacon Biomedical, LLC, Jupiter, FL (US)

(72) Inventor: Dale Mitchell, Jupiter, FL (US)

(73) Assignee: Beacon Biomedical, LLC, Jupiter, FL (US)

( * ) Notice: Subject to any disclaimer, the term of this patent is extended or adjusted under 35 U.S.C. 154(b) by 103 days.

(21) Appl. No.: 13/958,163

(22) Filed: Aug. 2, 2013

(65) Prior Publication Data

US 2014/0039626 A1 Feb. 6, 2014

Related U.S. Application Data

(60) Provisional application No. 61/678,891, filed on Aug. 2, 2012.

(51) Int. Cl.
  *A61F 2/44* (2006.01)
  *A61F 2/46* (2006.01)
  (Continued)

(52) U.S. Cl.
  CPC .............. *A61F 2/4611* (2013.01); *A61F 2/447* (2013.01); *A61F 2/4455* (2013.01); *A61F 2002/2817* (2013.01); *A61F 2002/2835* (2013.01); *A61F 2002/3008* (2013.01); *A61F 2002/3083* (2013.01); *A61F 2002/30171* (2013.01); *A61F 2002/30255* (2013.01); *A61F 2002/30266* (2013.01); *A61F 2002/30286* (2013.01); *A61F 2002/30523* (2013.01); *A61F 2002/30538* (2013.01); *A61F 2002/30777* (2013.01); *A61F 2002/30785* (2013.01); *A61F 2002/30828* (2013.01); *A61F 2002/30904* (2013.01); *A61F 2002/448* (2013.01); *A61F 2002/4475* (2013.01);
  (Continued)

(58) Field of Classification Search
  CPC . A61F 2/44; A61F 2/4455; A61F 2002/4627; A61F 2002/30828; A61F 2002/3083; A61F 2002/448; A01B 12/006
  USPC .............................. 623/17.11–17.16; 606/99
  See application file for complete search history.

(56) References Cited

U.S. PATENT DOCUMENTS 5,989,289 A  11/1999  Coates et al.
6,368,351 B1  4/2002  Glenn et al.
(Continued)

FOREIGN PATENT DOCUMENTS

WO  WO2008036636  3/2008
WO  WO2011056172  5/2011

*Primary Examiner* — Mary Hoffman
*Assistant Examiner* — Tara R Carter
(74) *Attorney, Agent, or Firm* — McHale & Slavin, P.A.

(57) ABSTRACT

A process for inserting a pivotable interbody spacer including an insertion instrument configured to manipulate a pivotable interbody spacer during insertion, wherein the insertion instrument includes means for coupling the interbody spacer and a means for fixing the angular position of the interbody spacer. According to one method for inserting an interbody spacer in a spinal disk space, the interbody spacer is grasped by the insertion instrument and fixed at a first angular position. The interbody spacer is next inserted into a surgical site. Next, the interbody spacer is released from a first angular position. Then, the insertion instrument is pivoted about a coupling of the interbody spacer such that the interbody spacer is in a second angular position. The angular position of the interbody spacer is then fixed in the second angular position. This insertion process continues until the interbody spacer is positioned in the desired location.

13 Claims, 11 Drawing Sheets

(51) Int. Cl.
 *A61F 2/30* (2006.01)
 *A61F 2/28* (2006.01)

(52) U.S. Cl.
 CPC . *A61F 2002/4622* (2013.01); *A61F 2002/4623* (2013.01); *A61F 2002/4627* (2013.01); *A61F 2310/00017* (2013.01); *A61F 2310/00023* (2013.01)

(56) References Cited

U.S. PATENT DOCUMENTS

| | | |
|---|---|---|
| 6,530,929 B1 | 3/2003 | Justis et al. |
| 6,599,294 B2 | 7/2003 | Fuss et al. |
| 6,696,073 B2 | 2/2004 | Boyce et al. |
| 6,719,794 B2 | 4/2004 | Gerber et al. |
| 6,830,570 B1 | 12/2004 | Frey et al. |
| 6,942,697 B2 | 9/2005 | Lange et al. |
| 6,974,480 B2 | 12/2005 | Messerli et al. |
| 7,018,413 B2 | 3/2006 | Kruger |
| 7,041,137 B2 | 5/2006 | Fulton et al. |
| 7,060,073 B2 | 6/2006 | Frey et al. |
| 7,188,626 B2 | 3/2007 | Foley et al. |
| 7,520,879 B2 | 4/2009 | Justis et al. |
| 7,892,239 B2 | 2/2011 | Warnick et al. |
| 8,043,293 B2 | 10/2011 | Warnick |
| 8,157,845 B2 | 4/2012 | Warnick et al. |
| 8,444,650 B2 | 5/2013 | Warnick et al. |
| 2003/0100950 A1* | 5/2003 | Moret .................. 623/17.16 |
| 2003/0139813 A1 | 7/2003 | Messerli et al. |
| 2004/0097929 A1 | 5/2004 | Branch et al. |
| 2004/0199251 A1 | 10/2004 | McCombe et al. |
| 2005/0131536 A1 | 6/2005 | Eisermann et al. |
| 2005/0228500 A1 | 10/2005 | Kim et al. |
| 2005/0277934 A1 | 12/2005 | Vardiman |
| 2006/0004453 A1* | 1/2006 | Bartish et al. .............. 623/17.15 |
| 2006/0229627 A1 | 10/2006 | Hunt et al. |
| 2006/0241761 A1 | 10/2006 | Gately |
| 2007/0078460 A1 | 4/2007 | Frigg et al. |
| 2007/0162128 A1 | 7/2007 | DeRidder et al. |
| 2007/0213737 A1* | 9/2007 | Schermerhorn et al. ........ 606/86 |
| 2007/0213826 A1 | 9/2007 | Smith et al. |
| 2008/0009880 A1 | 1/2008 | Warnick et al. |
| 2008/0091211 A1* | 4/2008 | Gately .......................... 606/99 |
| 2008/0140085 A1 | 6/2008 | Gately et al. |
| 2008/0221694 A1 | 9/2008 | Warnick et al. |
| 2008/0306488 A1 | 12/2008 | Altarac et al. |
| 2012/0010717 A1 | 1/2012 | Spann |

\* cited by examiner

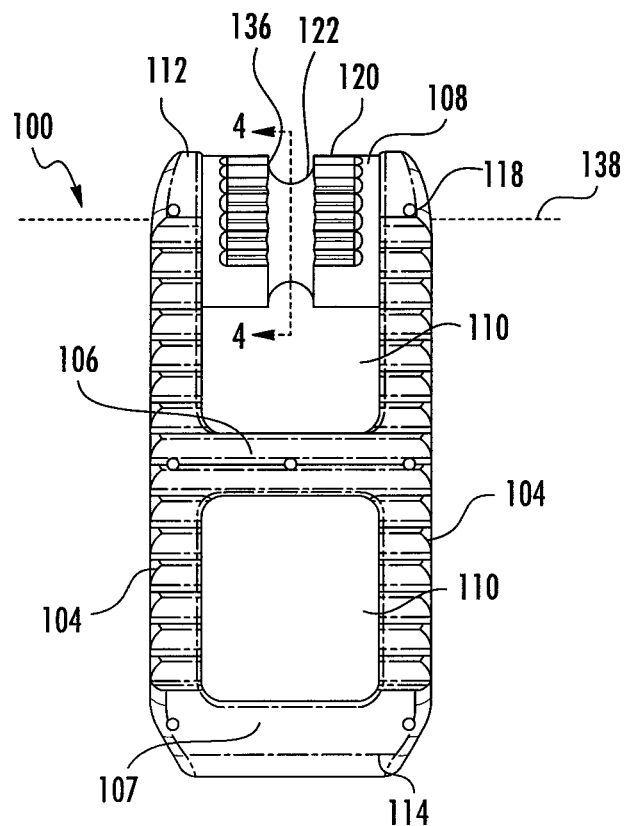
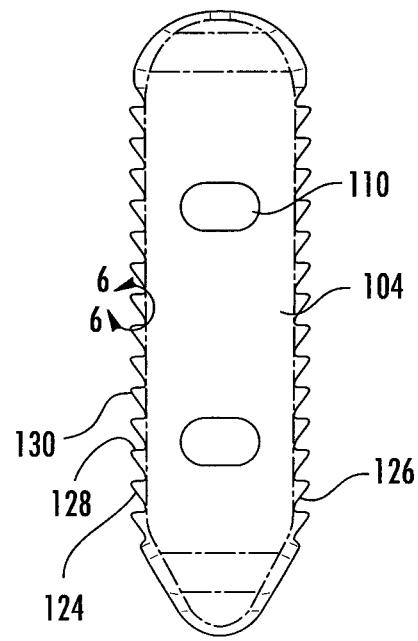
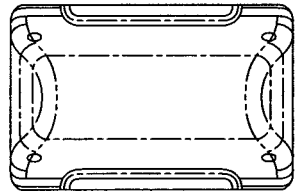
FIG. 1
FIG. 2
FIG. 3

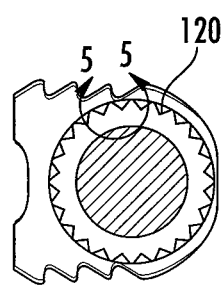 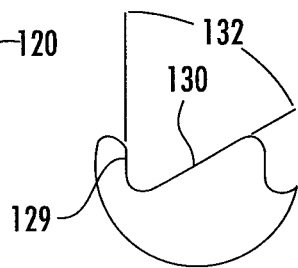
FIG. 4   FIG. 5   FIG. 6

PIVOTAL LATERAL CAGE AND METHOD OF INSERTION

CROSS REFERENCE TO RELATED APPLICATIONS

In accordance with 37 C.F.R. 1.76, a claim to priority is included in the Application Data Sheet filed concurrently herewith. Accordingly, the present invention claims priority under 35 U.S.C. 119(e), 120, 121 and 365(c) to U.S. Provisional Application Ser. No. 61/678,891; filed on Aug. 2, 2012, entitled, "PIVOTAL LATERAL CAGE AND METHOD OF INSERTION", which is a continuation-in-part of U.S. Pat. No. 8,444,650, issued May 21, 2013, entitled, "PIVOTABLE INTERBODY SPACER SYSTEM AND METHOD", which is a continuation of U.S. Pat. No. 7,892,239, issued Feb. 22, 2011, entitled "PIVOTABLE INTERBODY SPACER SYSTEM AND METHOD"; and U.S. Pat. No. 8,157,845, issued Apr. 17, 2012, entitled "PIVOTABLE VETREBRAL SPACER", which are continuation-in-part applications of U.S. Pat. No. 8,043,293, issued Oct. 25, 2011, entitled "PIVOTABLE INTERBODY SPACER", which claims priority under 35 U.S.C. §119(e) to U.S. Provisional Application No. 60/784,546; filed Mar. 22, 2006, entitled, "PIVOTAL INTERBODY SPACER", the entireties of which are incorporated herein by reference.

FIELD OF THE INVENTION

The present invention and method of use relate to bone fixation devices and procedures for the placement of these devices in an individual. More particularly, the present invention relates to a system and method of inserting a spinal implant for spinal fusion.

BACKGROUND OF THE INVENTION

The degeneration of the intervertebral disk, in particular, the degeneration of the nucleus pulposus, results in a loss of height in the affected disk space which is associated with a weakening of the annulus fibrosus and of the ligaments. As a consequence, the spinal column becomes instable and is more susceptible to horizontal displacement of the vertebral bodies with respect to one another. This horizontal movement of the vertebral bodies results in impairments of the nerve roots in this region and/or of the spinal marrow, and in pain resulting from these impairments.

The principle treatment of these symptoms consists of the surgical removal of the nucleus pulposus and the insertion of support bodies in order to restore the normal height of the disk space. There are a variety of demands on both the surgeon performing an intervertebral procedure, and on the spinal spacers themselves.

A Transforaminal Lumbar Interbody Fusion (TLIF) is a surgical procedure that uses a posterior and lateral approach to access the disc space. To gain access to the disc space, typically a facet joint is removed and access is gained via the nerve foramen. While more technically demanding of the surgeon than other fusion techniques, a TLIF offers a number of clinical advantages. Specifically, when compared to a PosteroLateral Fusion (PLF), a TLIF approach leaves much more of the soft tissue intact, which is less traumatic for the patient. Further, a PLF does not provide sufficient access to the disc space for comprehensive evacuation of the disc.

While Posterol Lateral InterBody Fusion (PLIF) provides limited access to the disc space, a TLIF approach also provides access to the interbody space, but without the need for manipulation of neural elements, reducing the risk of postoperative neural deficit. Additionally, in TLIF, only a single spacer is placed. More specifically, the TLIF spacer is placed in the anterior aspect of the disc space, thus providing space for a substantial fusion mass in the posterior aspect of the disc space where the natural compression occurs.

Traditional TLIF procedures do, however, suffer from shortcomings. For example, to place the desired spacer in the anterior aspect of the disc space from an oblique posterior approach, traditional procedures demand that the spacer be released from the inserter and then tamped into place. This two step insertion of the spacer is generally recognized among surgeons as cumbersome. The problem of manipulating the spacer into the disc space may be exacerbated in patients where the iliac crest must be maneuvered around to place the implant.

Therefore, there is a need for a device, system and procedure to enable access to the area between the Lumbar spine, the L-2, and the Sacrum, the S1, from a lateral or posteriolateral approach. The system should provide insertion tooling that cooperates with an implant to allow a surgeon to pivot/orient the implant with respect to the insertion tool without fully releasing control of the implant. The system should allow the surgeon to positively re-engage/lock the implant to the insertion tool once the desired angle between the inserter and implant has been achieved. The release for rotation and re-locking of the implant with respect to the insertion tool should be repeatable as often as desired or needed by the surgeon. The insertion tool should be self contained and should not require excessive strength to operate.

SUMMARY OF THE INVENTION

A preferred embodiment of the present invention discloses a unique method of pivotably implanting an interbody spacer between the vertebrae of the Lumbar spine, the L-2, and the Sacrum, the S1, while avoiding the ilium.

Accordingly, it is an objective of the present invention to disclose a unique method of pivotably implanting an interbody spacer between the lowest vertebrae of the Lumbar spine, the L-2, and the Sacrum, the S1.

It is a further objective of the present invention to provide a pivotable interbody spacer which includes a body defining an inner cavity and a plurality of teeth formed on one end of said spacer.

It is yet another objective of the present invention to provide a pivotable interbody spacer system which includes a spacer including a body defining an inner cavity and a plurality of teeth formed on one end of the spacer, and an insertion instrument associated with the spacer, wherein the insertion instrument includes a retractable latching mechanism and matching interior teeth configured to pivotably mate with said teeth formed on said spacer.

It is still a further objective of the present invention to provide a unique procedure to insert an interbody spacer between the L-2 and S-1 by employing an optimal angle for insertion which would enable insertion of the interbody spacer with minimal disturbance of soft tissue.

It is still a further objective of the present invention to provide a method for pivotably implanting an interbody spacer which includes coupling the spacer to a pivoting instrument, inserting the spacer through a nerve foramen, simultaneously pivoting and inserting the spacer until the spacer is inserted to its final position, and releasing the spacer from the instrument to facilitate removal of the instrument.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 1 is a top view of a pivotable interbody spacer, according to one exemplary embodiment;

FIG. 2 is a side view of the embodiment illustrated in FIG. 1;

FIG. 3 is an end view of the embodiment illustrated in FIG. 1;

FIG. 4 is a section view taken along lines 4-4 of FIG. 1;

FIG. 5 is a section view taken along lines 5-5 of FIG. 4;

FIG. 6 is a section view taken along lines 6-6 of FIG. 2;

DETAILED DESCRIPTION OF THE INVENTION

Figure 7:
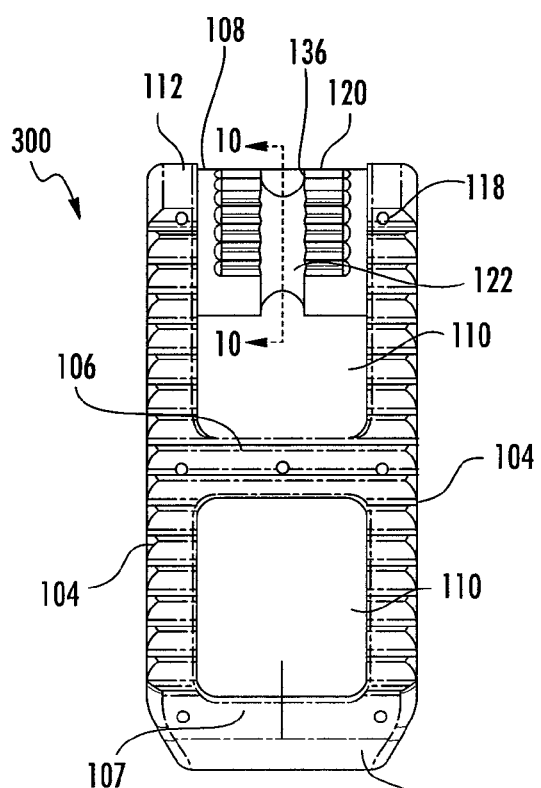
FIG. 7 is a top view of an alternative embodiment of the interbody spacer having an angled profile for correction of spinal deformities.
Figure 8:
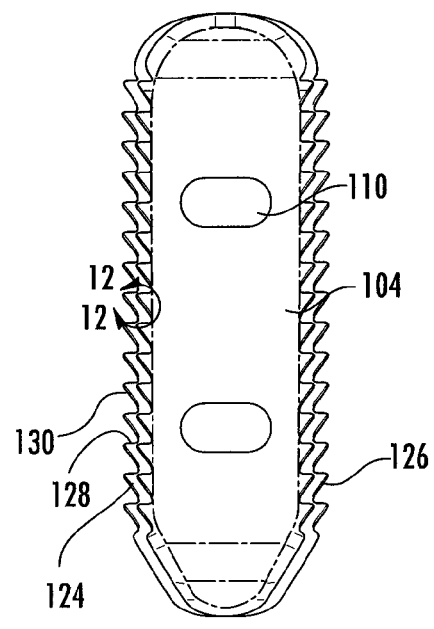
FIG. 8 is a side view of the embodiment illustrated in FIG. 7.
Figure 9:
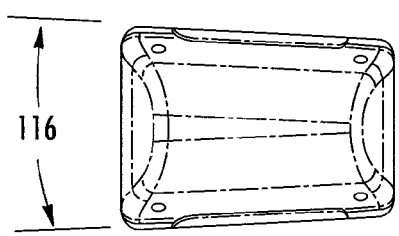
FIG. 9 is an end view of the embodiment illustrated in FIG. 7.
Figure 10:
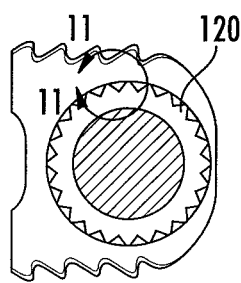
FIG. 10 is a section view taken along lines 10-10 of FIG. 7.
Figure 11:
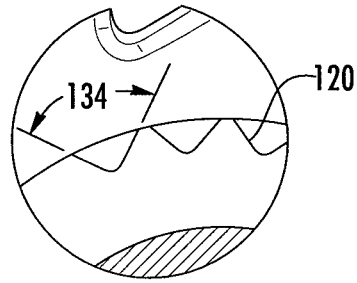
FIG. 11 is a section view taken along lines 11-11 of FIG. 10.
Figure 12:
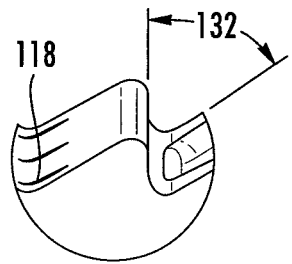
FIG. 12 is a section view taken along lines 12-12 of FIG. 8.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

Figure 13:
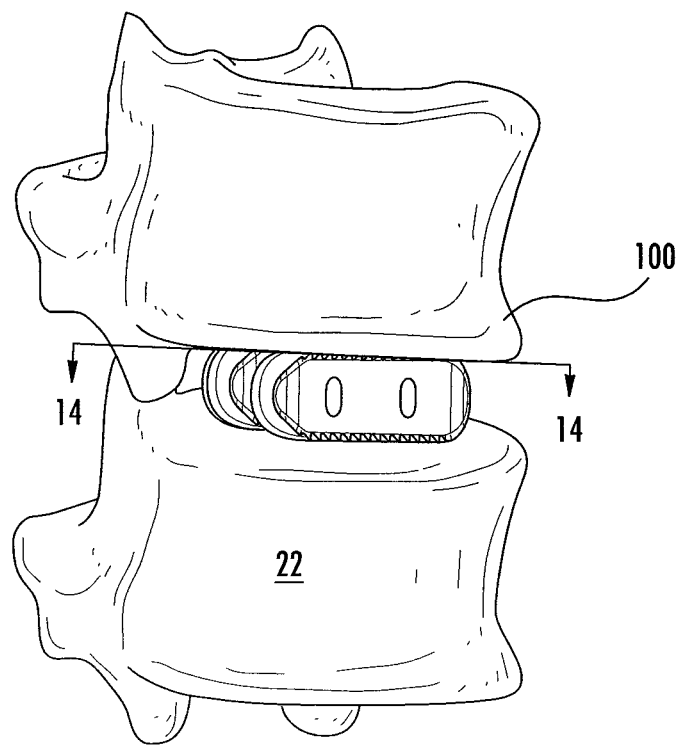
FIG. 13 is a perspective view of a spinal section, illustrated with an interbody spacer in the disc space.

Referring to FIGS. 1-6, which are now referenced, one embodiment of the interbody spacer (100) is illustrated. As illustrated, the present exemplary interbody spacer is designed for use as an intervertebral spacer in spinal fusion surgery, where portions of an affected disc are removed from between two adjacent vertebrae 102 and replaced with an interbody spacer (100) that provides segmental stability, may correct a deformity, and allows for bone to grow between the two vertebrae to bridge the gap created by disk removal (FIG. 13).

As shown, the present exemplary interbody spacer (100) has a generally rectangular shape comprised of a pair of side rails (104), a pair of cross supports (106) and a transverse spindle (108) to facilitate the insertion of the interbody spacer through a narrow approach window into the disk space. As illustrated, the present interbody spacer (100) includes a proximal end (112) that will be closest to a surgeon during use, and a distal end (114) that will likely be the leading edge of insertion during use. In general, the proximal end (112) is constructed and arranged for connection to an insertion tool that allows the interbody spacer to be grasped or locked into a specific orientation with respect to the insertion tool. In a most preferred embodiment, the insertion tool is constructed and arranged to include a grasping mode which allows rotation of the implant about a spindle axis 138, and a locking mode that allows the implant to be locked into the desired orientation once the implant is positioned in the desired orientation. This engagement is sufficiently rigid to allow the surgeon to strike the insertion tool when necessary without disturbing the orientation yet allows the surgeon to reposition the interbody spacer as many times as desired without completely releasing the implant by utilizing the grasping mode. The surgeon can thus switch between the grasp and the lock modes as many times as is necessary and the switching of modes can occur while the implant is positioned within the patients' anatomy. In the illustrated embodiment, the distal end (114) of the interbody spacer (100) has a double elliptical leading edge for ease of insertion through the overlying tissues and into the intervertebral space.

The central portion of the interbody spacer (100) may have a variety of apertures, bores and/or cavities (110) designed to facilitate and support bone growth. The apertures are particularly useful for containing bone growth enhancement materials such as, but not limited to, bone chips or fragments, bone morphogenic protein (BMP), bone cement, bioactive glass or the like. In this manner, the bone growth enhancement materials may be delivered directly to the disc space. According to one embodiment, the side rails and cross supports of the interbody spacer are hollowed out to increase cavity volume while maintaining surface area in contact with the bone to prevent the interbody spacer from impacting into the bone. Consequently, the present exemplary interbody spacer (100) employs geometry that provides for a compact interbody spacer with relatively large surface area and internal cavity (110). Other cavities and geometries may be included in the interbody spacer structure, such as a hollow transverse spindle (108).

According to one exemplary embodiment, the interbody spacer (100) has an upper face (124) and an opposing lower face (126). A series of ridges (128) traverse the upper and lower faces (124, 126). The ridges (128) are configured to facilitate the insertion of the interbody spacer (100) by preventing retrograde motion and slippage during the insertion process. After the surgery is complete, the ridges (128) also may provide increased surface area, encourage bone growth, and/or prevent dislocation of the interbody spacer (100). In a most preferred embodiment, each ridge (128) includes a substantially vertical face (129) and an angled face (130) wherein the included angle (132) between the two faces is about sixty degrees. This construction allows the interbody spacer to be easily pushed or tamped into position while resisting rearward migration. Included angles (132) of greater than or less than sixty degrees may be utilized without departing from the scope of the invention. The upper and lower faces (124, 126) may also include a plurality of radiopaque markers (118) which aid the surgeon in positioning the implant. In a preferred embodiment, two markers are positioned relative to the transverse spindle (108), three markers relative to the center cross support (106) and two relative to the leading cross support (107).

Additionally, as illustrated in FIGS. 1, 4 and 5, the present interbody spacer (100) includes a plurality of teeth (120) or other frictionally engaging features extending around the periphery of the spindle (108). The teeth are utilized to provide various angles of engagement between the insertion tool (200) and the interbody spacer and allow for the insertion instrument to firmly grip the interbody spacer (100) and aid its manipulation during insertion. This construction provides numerous advantages when the surgeon is maneuvering around a structure such as the iliac crest while utilizing a lateral or posteriolateral approach to place the interbody spacer into a disc space in the lower back which may require the surgeon to alter the angle between the insertion tool and the interbody spacer numerous times. The teeth (120) of a most preferred, but non-limiting, embodiment are formed to have an elongated V-shape and have an included angle (134) of about ninety degrees. The teeth may be formed to any depth and width suitable to provide the surgeon with the desired number of indexed engagements to the insertion tool for a particular procedure. It should also be noted that while V-shaped teeth are illustrated, any shape suitable for providing the locking engagement to the insertion tool may be utilized without departing from the scope of the invention. As described above, the teeth (120), when coupled with an appropriate insertion instrument, may simplify a surgical procedure by allowing the pivoting and tamping of the interbody spacer (100) without having to release it from the grasp of the insertion instrument. In at least one embodiment, the spindle (108) includes a friction barrel (122). The friction barrel is constructed and arranged for grasping by the insertion tool while still allowing rotation of the interbody spacer (100) about the axis created by the spindle. In a most preferred embodiment, the friction barrel includes side surfaces (136) that provide longitudinal alignment with the insertion tool while in the grasping mode. The friction barrel can be sized to require a predetermined amount of force to rotate the interbody spacer while the insertion tool is in a grasping mode. This prevents the interbody spacer from rotation due to gravity or an errant bump against the patients' anatomy during surgery, and allows the surgeon to precisely orient the interbody spacer as desired for implantation. The interbody spacer 100 is preferably constructed from biocompatible material such as polyetheretherketone (PEEK), polyaryletherketone (PEAK), stainless steel, titanium or the like.

Referring to FIGS. 7-12, an alternative embodiment of the interbody spacer 300 is illustrated. This embodiment is similar to the embodiment illustrated in FIGS. 1-6 with the exception that the upper and lower faces (124, 126) are arranged to include a face angle 116 with respect to each other so that one side rail (104) is taller than the other. This construction allows the surgeon to correct spinal deformities such as lordosis, scoliosis or the like.

Figure 14:
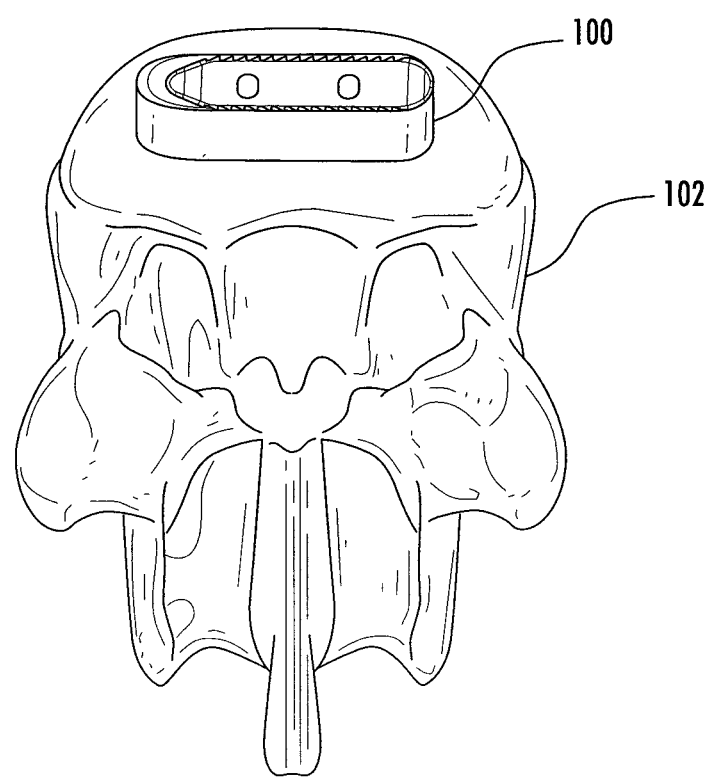
FIG. 14 is a section view taken along lines 14-14 of FIG. 13.

Referring to FIGS. 13 and 14, the interbody spacer (100) is illustrated in position between a pair of vertebrae (102). While the present interbody spacer may be utilized anywhere along the spine, the axis of rotation along the centerline of the transverse spindle (108) makes the device particularly suited for use in the lower spine, most particularly between the L-2 and S-1 disc spaces. FIG. 14 is a partial perspective view of FIG. 13 illustrated with the upper vertebrae removed for clarity further illustrating the positioning and the cooperation between the upper and lower faces (124, 126) with the bone.

Referring to FIGS. 15-20, an insertion tool or instrument (200) suitable for use with the interbody spacer (100) is illustrated. The insertion tool (200) includes a handle (210) configured to facilitate manual grasping of the insertion tool (200), a lever (220) pivotably connected to the handle (210), and a hollow shaft (230) extending from one end of the handle (210). At a distal end of the shaft (230) a number of features are disposed which facilitate the grasping and subsequent manipulation of the pivotable interbody spacer (100), according to one exemplary embodiment. Also within the shaft is a tie rod (232) connected between opposing jaws (240, 250) and lever (220). An impaction cap (206) is located on the end of the handle (210). The impaction cap (206) provides a durable and resilient surface for impacting the insertion tool with a hammer or the like to tamp the interbody spacer (100) into position.

Figure 17:
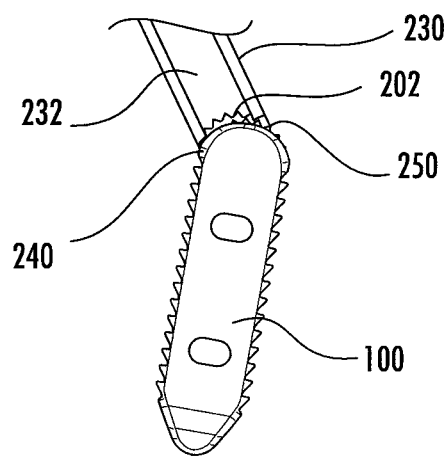
FIG. 17 is a partial perspective view illustrating the connection between the interbody spacer and the insertion tool.
Figure 18:
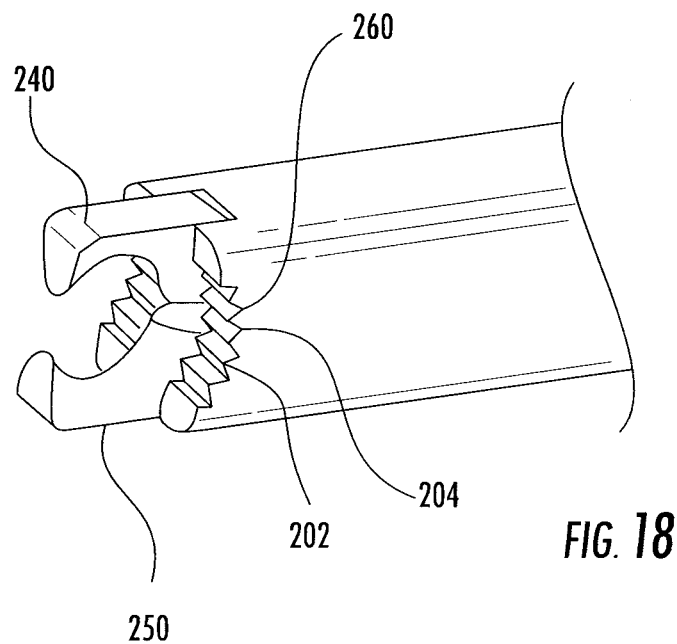
FIG. 18 is a partial perspective view of one embodiment of the gripping end of the insertion tool.

As shown in FIGS. 17 and 18, the shaft (230) terminates in features configured to facilitate the grasping and subsequent manipulation of the interbody spacer (100) including opposing jaws (240, 250) and frictional features designed to engage with the interbody spacer (100). In a particularly desirous embodiment, the distal end of the shaft (230) has a concave surface (204) with a plurality of teeth (260) that is configured to receive and engage the plurality of teeth (120) disposed about the perimeter of the convex spindle surface of the proximal end (112) of the interbody spacer (100). In one exemplary embodiment, the jaws can pass onto the friction barrel (122) of the spindle (108) and between the friction barrel side surfaces (136) to couple the interbody spacer (100) to the insertion tool (200). This construction allows the tool to grasp the interbody spacer while maintaining axial alignment with the tool and allowing rotation of the interbody spacer as desired by the surgeon.

Figure 15:
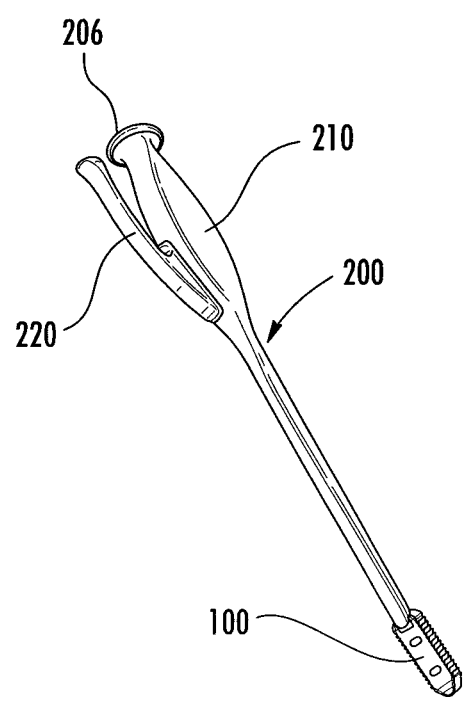
FIG. 15 is a perspective view of an insertion instrument configured to grasp and manipulate the pivotable interbody spacer of the present invention.

FIGS. 15-17, 19 and 20 illustrate various views of an interbody spacer (100) coupled to an insertion tool (200). The lever (220) is mechanically connected through tie rod (232) to the opposing jaws (240, 250) at the terminal end of the shaft (230). The lever (220) can be moved into three positions that correspond to three different jaw configurations. In FIG. 15, the lever (220) is shown in a first position that corresponds to an open jaw configuration. As shown in FIG. 18, in the open jaw configuration, the first jaw (240) and the second jaw (250) are extended out of the shaft body and apart from each other. In this open configuration, the jaws can pass onto the friction barrel (122) and around the outer perimeter of the transverse spindle (108). The spacing between the jaws (240, 250) can be such that the jaws (240, 250) pass around the perimeter of the friction barrel (122) without substantial resistance, or such that the interbody spacer "snaps" into the internal cylindrical space created between the jaws (240, 250).

Figure 16:
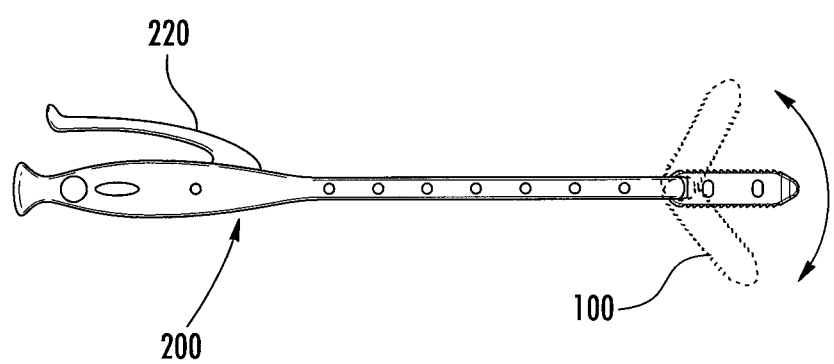
FIG. 16 is a perspective view, illustrating controlled manipulation of the interbody spacer using the insertion instrument.

FIG. 16 illustrates a side view of the insertion tool (200) and the interbody spacer (100) having the lever (220) in a second position which corresponds to a grasping jaw configuration. In the grasping jaw configuration, the opposing jaws (240, 250) are brought together around the outer perimeter of the friction barrel (122). The interbody spacer (100) is firmly grasped by the jaws (240, 250) in a manner that still allows the outer perimeter of the friction barrel (122) to rotate within the internal space created by the closed jaws (240, 250) without allowing the interbody spacer (100) to be disengaged from the insertion tool (200).

Figure 19:
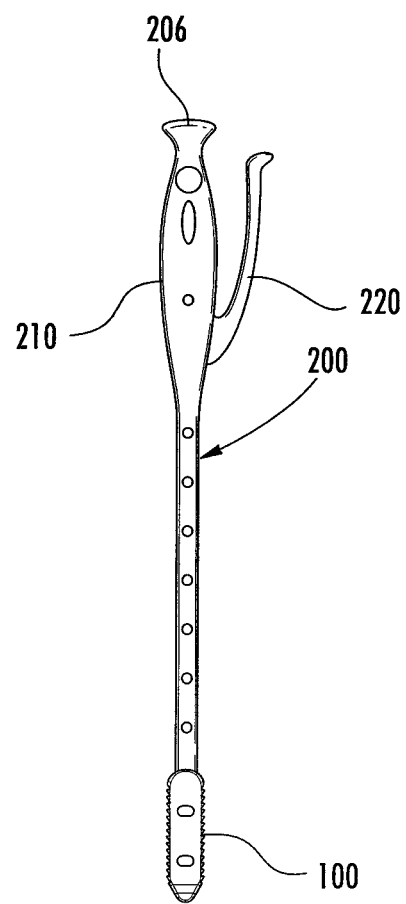
FIG. 19 is a perspective view of the interbody spacer and the insertion tool.
Figure 20:
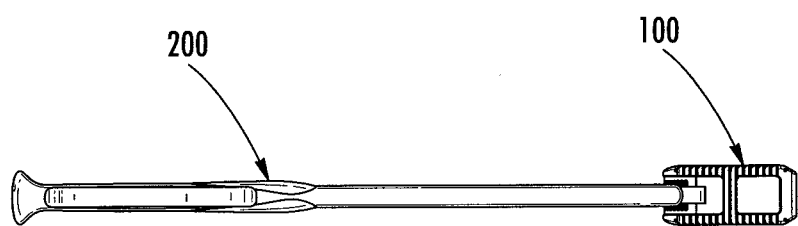
FIG. 20 is a front view of the interbody spacer and insertion tool.

FIGS. 15, 19 and 20 illustrate perspective, side and top views of the insertion instrument (200) and the interbody spacer (100) having the lever in a third locked position which further restrains the interbody spacer (100) by locking its rotation. This is particularly useful during impaction of the interbody spacer (100) into position in the intervertebral space. In one exemplary embodiment, the third lever position corresponds to a closed and retracted jaw configuration. In the closed and retracted jaw configuration the opposing jaws (240, 250) are brought together around the outer perimeter of the friction barrel (122) and the jaws (240, 250) are retracted into the shaft (230) such that the frictional features on the spindle, e.g. teeth (202) engage the corresponding teeth (120) on the interbody spacer. The engagement of the frictional features prevents the pivoting of the interbody spacer (100) with the jaws (240, 250). For example, while the lever (220) is in the second position, the interbody spacer (100) can be pivoted into the desired angular position with respect to the insertion instrument (200). Then, with the interbody spacer (100) at the desired angle, the lever (220) is moved into a third position which retracts the jaws into the shaft, thereby engaging the teeth (202) with interbody spacer teeth (120). The interbody spacer (100) is firmly grasped by the jaws (240, 250) and locked at the desired angle by the engagement of the mating teeth (120, 202). The interbody spacer (100) can now be impacted into the disc space. The position and motion of the rigidly held interbody spacer (100) can be precisely controlled by manipulating the insertion instrument (200).

A unique method of inserting an interbody spacer using an insertion tool is described hereinafter with reference to interaction between the interbody spacer as described in the figures. The present method begins by the insertion instrument engaging the interbody spacer as shown in FIGS. 16-18. To initially engage the interbody spacer, the lever 220 is moved to the first position as shown in FIG. 15. This opens the opposing jaws (240, 250) as shown in FIG. 18. The jaws (240, 250) are then inserted onto the friction barrel (122). Once the instrument is engaged to the interbody spacer, the lever can be moved to the third position to lock the interbody spacer at the desired orientation. This closes and retracts the jaws (240, 250), which pulls the teeth (120) into engagement with teeth (202), thereby restraining the interbody spacer (100) from pivoting with respect to the insertion instrument (200).

The insertion instrument with the attached interbody spacer (100) is then inserted into the surgical site, allowing the surgeon to reposition the interbody spacer as many times as desired without releasing the interbody spacer. In one exemplary embodiment, the interbody spacer is placed in the anterior space between adjoining vertebral bodies by the TLIF process. However, the present system and method may be used for any number of implant applications. As mentioned above, the TLIF process uses a posterior, posteriolateral and lateral approach to access the disc space. The interbody spacer (100) enters the surgical site with the distal end (114) leading. As mentioned above, the distal end (114) has a double elliptical shape, which eases the insertion of the interbody spacer into the surgical site. The interbody spacer (100) may be inserted using a combination of simultaneous impaction and rotation, followed by repositioning of the instrument about the implant. Impaction typically involves striking the impaction cap (206) on the end of handle, either manually or with another instrument. Once the interbody spacer (100) can no longer be inserted in its coupled state, the instrument may be repositioned or pivoted relative to the interbody spacer (100) to allow for further insertion and simultaneous rotation. To pivot the insertion instrument (200) about the end of the interbody spacer, the lever is moved to the second position which disengages the matching teeth (120, 202). The insertion instrument can then be pivoted with respect to the partially inserted interbody spacer (100). The lever (220) is then returned to the third position. By pivoting the interbody spacer (100), obstacles can be avoided, and narrow or non-linear passageways can be followed without tamping the interbody spacer into place. If required, the interbody spacer can then be further inserted by impacting the insertion instrument. The steps of pivoting and inserting the interbody spacer are continued until the interbody spacer is in its final position. Once in a final position, the interbody spacer (100) is released from the insertion instrument (200) by moving the lever to the first position. The jaws (240, 250) open and can then be disengaged from around the outer perimeter of the friction barrel (122). The insertion instrument (200) is removed from the patient, leaving the interbody spacer correctly positioned within the surgical site as illustrated in FIGS. 13 and 14.

The present exemplary device and unique method provide for a pivotable interbody spacer that provides a user with the ability to insert the interbody spacer in a non-linear path. The insertion instrument can lock onto the interbody spacer at multiple angles to allow for the interbody spacer to be pivoted in increments if the instrument rotation is restricted such that the instrument can only be rotated less than the total rotation required to position the interbody spacer. This additional surgical flexibility can allow insertion of the interbody spacer with the removal of less tissue and bone which results in less invasive surgery, fewer post operative complications, and quicker patient recovery time. This also permits access to the L-2, S-1 site while avoiding the ilium by employing an optimal angle of approach.

The present exemplary interbody spacer (100) further employs geometry that provides for a small interbody spacer with relatively large surface area and internal cavity. The interbody spacer is hollowed out to increase cavity volume and surface area while minimizing overall size. Additionally, the present exemplary systems and methods allow for rotation of the interbody spacer for final positioning without having to release the interbody spacer and tamp the interbody spacer into place. Because the insertion instrument is not required to be disengaged from the interbody spacer, quicker and simpler surgeries are possible.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A surgical kit comprising:

an interbody spacer (100) said interbody spacer including an upper face (124) and an opposing lower face (126), a pair of side rails (104), an integrally formed spindle (108) extending transversely and connecting said side rails at a proximal end (112), said spindle including a friction barrel portion a center cross support (106) connecting said side rails at a central portion and a leading cross support (107) connecting said side rails at a distal end 114 of said interbody implant, said spindle (108) including a plurality of teeth (120) or other frictionally engaging features extending around the periphery thereof, said teeth arranged about an axis of rotation (138) extending through said transverse spindle (108) to provide various angles of engagement between an insertion tool (200) and said interbody spacer (100);

an insertion tool (200) for use with said interbody spacer (100), said insertion tool (200) including a handle (210) configured to facilitate manual grasping thereof, a distal end of said insertion tool being constructed and. arranged for grasping said spindle and subsequent manipulation of said pivotable interbody spacer (100), said manipulation including the ability to rotate said interbody spacer with respect to said insertion tool about said axis of rotation (138) without releasing said interbody spacer, said distal end including a pair of opposing jaws (240, 250) which can be moved into three distinct positions that correspond to three different jaw configurations for enclosing and grasping said friction barrel, a first position corresponds to an open jaw configuration whereby a first jaw (240) and a second jaw (250) are extended out of said insertion tool and apart from each other so that said jaws can pass onto said friction barrel (122) and around an outer perimeter of said transverse spindle (108) without substantial resistance, a second position corresponds to an enclosing and grasping jaw configuration, whereby said opposing jaws (240, 250) are brought together around the outer perimeter of said friction barrel (122) whereby said spindle of said interbody spacer (100) is enclosed and firmly grasped by said jaws (240, 250) in a manner that still allows the outer perimeter of said friction barrel (122) to rotate within the internal space created by the closed jaws (240, 250) without allowing the interbody spacer (100) to be disengaged from the insertion tool (200), and a third position corresponds to a locked jaw configuration, whereby said opposing jaws (240, 250) are brought together around the outer perimeter of said friction barrel (122) and said jaws (240, 250) are retracted into said insertion tool such that a structural feature of said interbody spacer interlocks with a portion of said insertion tool such that the interlocking prevents the pivoting of said interbody spacer (100) with respect to said insertion tool (200).

2. The surgical kit of claim 1 wherein said friction barrel (122) includes at least one side surface (136), said at least one side surface providing longitudinal alignment, between said insertion tool and said interbody implant when grasped by said insertion tool (200).

3. The surgical kit of claim 1 wherein said insertion tool includes a lever (220) pivotably connected. to said handle (210), and a hollow shaft (230) extending from said handle (210) a tie rod (232) extending through said hollow shaft, a first end of said tie rod (232) secured to said lever and a second end of said tie rod secured to said pair of opposing jaws (240, 250).

4. The surgical kit of claim 3 wherein said distal end of said shaft (230) has a concave surface (204) with a plurality of teeth (260) that is configured to receive and engage the plurality of teeth (120) disposed about the perimeter of the convex spindle surface of the proximal end (112) of the interbody spacer (100).

5. The surgical kit of claim 3 wherein said lever (220) can be moved into three distinct positions that correspond to said three different jaw configurations.

6. The surgical kit of claim 5 wherein a first position of said lever (220) corresponds to said open jaw configuration such that said interbody spacer (100) snaps into an internal cylindrical space created between said jaws (240, 250).

7. The surgical kit of claim 5 wherein a second position of said lever (220) corresponds to said grasping jaw configuration.

8. The surgical kit of claim 7 wherein said cooperation between said friction barrel (122) and said jaws (240, 250) is constructed and arranged to require a predetermined amount of force to cause rotation of said interbody spacer while said insertion tool (200) is in said grasping jaw configuration.

9. The surgical kit of claim 5 wherein a third position of said lever (220) corresponds to said locked jaw configuration.

10. The surgical kit of claim 1 wherein said upper and lower faces (124, 126) of said interbody spacer (100) include a face angle 116 with respect to each other so that one said side rail (104) is taller than the other said side rail (104).

11. The surgical kit of claim 1 wherein a series of ridges (128) traverse said upper and lower faces (124, 126), said ridges (128) configured to facilitate the insertion of said interbody spacer (100) by preventing retrograde motion and slippage during insertion thereof.

12. The surgical kit of claim 1 wherein each said ridge (128) includes a substantially vertical face (129) and an angled face (130) wherein the included angle (132) between the two faces is about sixty degrees.

13. The surgical kit of claim 1 wherein said upper and lower faces (124, 126) include a plurality of radiopaque markers (118) which aid the surgeon in positioning said interbody spacer (100).

* * * * *